(12) United States Patent
Woudenberg

(10) Patent No.: US 6,548,710 B2
(45) Date of Patent: Apr. 15, 2003

(54) PROCESS FOR PREPARING 1-INDANONES

(75) Inventor: Richard Herman Woudenberg, Elst (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/999,368

(22) Filed: Oct. 31, 2001

(65) Prior Publication Data

US 2002/0077507 A1 Jun. 20, 2002

Related U.S. Application Data

(60) Provisional application No. 60/252,681, filed on Nov. 21, 2000.

(30) Foreign Application Priority Data

Oct. 31, 2000 (EP) ............................................. 00203761

(51) Int. Cl.[7] .......................... C07C 45/63; C07C 45/67; C07C 2/02
(52) U.S. Cl. ....................... 568/323; 568/327; 568/328; 585/532
(58) Field of Search ................................. 568/323, 327, 568/328; 585/532

(56) References Cited

U.S. PATENT DOCUMENTS 5,840,948 A 11/1998 Rohrmann et al. ............ 556/11

OTHER PUBLICATIONS

Guthrie et al, Can.J.Chem.,68(3),397–403 (1990).*
Lee et al, J.Chem.Soc.D,(14),860–861 (1970).*
International Search Report, dated Feb 1, 2001.
"Preparation of 1–Indanones from α–Bromoaralkyl Ketones" by Robert W. Layer and Ian R. MacGregor, in *Journal of Organic Chemistry*, vol. 21, 1956, pp. 1120–1123.
"Allied Compounds of Vitamin B1.X. Structure of N–substituted Dithiourethans" in *Chemical Abstracts*, vol. 48, No. 10, 1954, p. 5866.
"Kinetics of the Base–Catalyzed Decomposition of α–Hydroperoxy Ketones" by Yasuhiko Sawaki and Yoshiro Ogata, in *Journal of the American Chemical Society*, vol. 97, No. 24, 1975, pp. 6983–6989.

"Advanced Organic Chemistry:,Reaction, Mechanicsms, and Structure" by Jerry March, 1929, —Fourth Ed., published by John Wiley & Sons, Inc., pp. 534–1013.

* cited by examiner

*Primary Examiner*—Johann Richter
*Assistant Examiner*—Sikarl A. Witherspoon
(74) *Attorney, Agent, or Firm*—Richard P. Fennelly

(57) ABSTRACT

The present invention relates to a process for preparing 1-indanones of formula I:

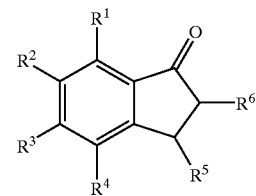

and isomers thereof, wherein $R^1$, $R^2$, $R^3$, $R^4$, $R^5$, and $R^6$ independently represent H or a $C_1$–$C_{20}$ hydrocarbon group or $R^1$ and $R^2$ or $R^2$ and $R^3$ or $R^3$ and $R^4$ and/or $R^5$ and $R^6$ together with the carbon atoms to which they are attached form a saturated or unsaturated 5- or 6-membered ring, said hydrocarbon group and/or said ring optionally containing one or more hetero atoms, said ring optionally being substituted with a $C_1$–$C_4$ hydrocarbon group, said process comprising reacting a compound of formula II:

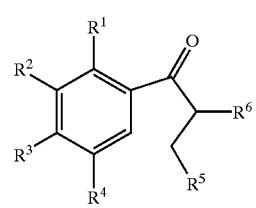

wherein $R^1$, $R^2$, $R^3$, $R^4$, $R^5$, and $R^6$ have the same meaning as defined above, with a chlorinating agent, followed by reaction with a Friedel-Crafts catalyst. The invention further relates to the preparation of the corresponding indenes.

10 Claims, No Drawings

PROCESS FOR PREPARING 1-INDANONES

The present application claims priority from European Patent Application No. 00203761.2, filed on Oct. 31, 2000 and from U.S. Provisional Application Ser. No. 60/252,681, filed Nov. 21, 2000.

The present invention relates to a process for preparing 1-indanones. It further pertains to the preparation of the corresponding indenes.

1-Indanones, which can be converted into the corresponding indene derivatives by known methods, are important intermediates in the synthesis of metallocene catalysts which typically are used in combination with a co-catalyst such as methylaluminoxane for the (co)polymerization of ethylenically unsaturated monomers, e.g., the production of isotactic polypropylene.

Several processes for preparing 1-indanones which start from either a propionic acid or an acrylic acid derivative are known in the art, but none of the prior art documents describe the process of the present invention.

For example, U.S. Pat. No. 5,840,948 describes a one-step process for preparing 1-indanones from benzene or a derivative thereof and a derivative of propionic acid carrying a leaving group in the (x-position using a Friedel-Crafts catalyst. The starting materials in this process typically contain two halogen atoms, preferably bromine or chlorine. In all examples, a dibrominated propionic acid derivative is used.

A disadvantage of the process of U.S. Pat. No. 5,840,948 is that the bromine or hydrobromic acid which results from the reaction presents a waste problem in terms of the presence and the amount of bromine-containing products.

DE 19637128 describes the reaction of an indane or tetralin derivative with a substituted acryloyl halide using a Friedel-Crafts catalyst.

A disadvantage of the process described in DE 19637128 is that the acryloyl-containing starting material is sensitive to dimerization and polymerization and that it is toxic.

R. W. Layer and I. R. MacGregor in the *Journal of Organic Chemistry*, Vol. 21, 1956, pp. 1120–1123, describe a process for the preparation of 1-indanones from α-bromoaralkyl ketones. It is mentioned that α-bromoaralkyl ketones are used because they are readily available. In the examples, bromine is used for preparing the α-bromoaralkyl ketones.

As described above, the use of bromine and the formation of bromine-containing products presents a waste problem.

The process according to the present invention avoids these disadvantages, presents a solution to the waste problem, and allows for the preparation of 1-indanones in high yield and selectivity.

According to the present invention, a process is provided for preparing 1-indanones of formula I:

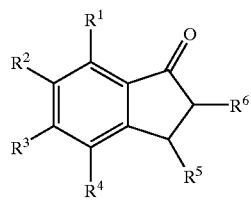

I and isomers thereof, wherein $R^1$, $R^2$, $R^3$, $R^4$, $R^5$, and $R^6$ independently represent H or a $C_1$–$C_{20}$ hydrocarbon group or $R^1$ and $R^2$ or $R^2$ and $R^3$ or $R^3$ and $R^4$ and/or $R^5$ and $R^6$ together with the carbon atoms to which they are attached form a saturated or unsaturated 5- or 6-membered ring, said hydrocarbon group and/or said ring optionally containing one or more hetero atoms, said ring optionally being substituted with a $C_1$–$C_4$ hydrocarbon group, said process comprising reacting a compound of formula II:

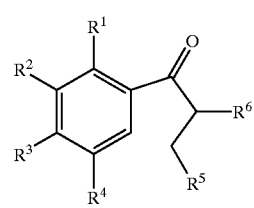

II wherein $R^1$, $R^2$, $R^3$, $R^4$, $R^5$, and $R^6$ have the same meaning as defined above, with a chlorinating agent, followed by reaction with a Friedel-Crafts catalyst.

It is to be noted that the regioselectivity of the ring closure reaction with the Friedel-Crafts catalyst is dependent on the presence or absence as well as the types of R-group substituents in the compound of formula II. It may be that more than one isomer is formed during this ring closure reaction, as can be seen in Example 3 described below. Hence, the invention process relates to 1-indanones of formula I and isomers thereof.

Suitable $C_1$–$C_{20}$ hydrocarbon groups include $C_1$–$C_{20}$ alkyl, $C_1$–$C_{10}$ alkoxy, $C_2$–$C_{20}$ alkenyl, $C_2$–$C_{20}$ alkynyl, $C_6$–$C_{20}$ aryl, $C_6$–$C_{20}$ aryloxy, $C_7$–$C_{20}$ arylalkyl, and $C_7$–$C_{20}$ alkylaryl groups, which groups optionally may contain one or more hetero atoms such as O, Si, and halogen atoms. Said groups may be linear or branched.

Preferably, $R^1$, $R^2$, $R^3$, $R^4$, $R^5$, and $R^6$ independently represent H or a $C_1$–$C_{20}$ alkyl group or $R^1$ and $R^2$ or $R^2$ and $R^3$ or $R^3$ and $R^4$ and/or $R^5$ and $R^6$ together with the carbon atoms to which they are attached form a saturated or unsaturated 5- or 6-membered ring, said ring optionally being substituted with a $C_1$–$C_4$ hydrocarbon group. More preferably, $R^1$, $R^2$, $R^3$, $R^4$, $R^5$, and $R^6$ independently represent H or a $C_1$–$C_4$ alkyl group or $R^1$ and $R^2$ or $R^2$ and $R^3$ or $R^3$ and $R^4$ and/or $R^5$ and $R^6$ together with the carbon atoms to which they are attached form a saturated or unsaturated 5- or 6-membered ring. Even more preferably, $R^1$, $R^4$, and $R^5$ represent H, $R^2$ and $R^3$ together with the carbon atoms to which they are attached form a saturated 5- or 6-membered ring, and $R^6$ represents H or a $C_1$–$C_4$ alkyl group. Most preferably, $R^6$ represents a $C_1$–$C_4$ alkyl group.

A particularly preferred $C_1$–$C_4$ alkyl group is a methyl group.

Suitable starting materials of formula II are either commercially available or can be prepared by methods known to a person skilled in this art, such as by Friedel-Crafts acylation.

In the context of the present invention, it is well-known to a person skilled in the art what is meant by the term "chlorinating agent." Chlorination of hydrocarbons is a common organic reaction and suitable chlorinating agents include chlorine, N-chlorosuccinimide, and sulfuryl chloride. For other suitable chlorinating agents the reader is referred to J. March, *Advanced Organic Chemistry*, Fourth Edition, John Wiley & Sons, New York, 1992, pp. 587–590. Preferred chlorinating agents are chlorine and sulfuryl chloride. In the process of the present invention most preferably sulfuryl chloride is used. Chlorine-containing salts that result from the chlorination reaction typically are discarded via the waste water. Surprisingly, the use of a chlorinating agent, in particular sulfuryl chloride, gave chlorinated products in a very high, nearly quantitative yield (see the Examples).

Typically, an acid or base catalyst in a conventional amount is used in the chlorination reaction. A practical acid catalyst is sulfuric acid, methanesulfonic acid or p-toluenesulfonic acid. A preferred chlorination catalyst is concentrated sulfuric acid.

Chlorination can be carried out in the absence or presence of a solvent. Suitable solvents include hydrocarbon solvents such as pentane, hexane, heptane, and toluene, and halogenated alkanes such as dichloromethane. Mixtures of solvents may also be used. Preferably, the reaction is carried out using a minimal amount of a solvent such as heptane.

An advantage of the present invention process is that it can be carried out at a relatively high concentration, which results in a higher reactor filling and a more economical process as compared to the processes of the prior art.

Chlorination can be carried out in a wide temperature range. Typically, it is performed at from 0° C. up to 100° C., preferably at from room temperature up to 100° C. A preferred temperature range for carrying out the chlorination at pilot plant scale (typically carried out in a 1,000 liters reactor) is 50 to 70° C.

Typically, the molar ratio of ketone (II) to chlorinating agent is 1:1 to 1:2. Preferably, it is 1:1 to 1:1.5, more preferably 1:1.1 to 1:1.2. Most preferably, a molar excess of about 10% of the chlorinating agent is used. Preferably, the excess of chlorinating agent is removed from the reaction product—in a conventional way, e.g., by evaporation or via destruction with water—before further reaction.

Typical reaction times for the chlorination reaction are in the order of 15 minutes to 4 hours.

In the invention process, the chlorination reaction is followed by a ring closure reaction using a Friedel-Crafts catalyst.

Suitable Friedel-Crafts catalysts are known in the art and are described, for example, in J. March, *Advanced Organic Chemistry*, Fourth Edition, pp. 535–542. Typically, these catalysts are Lewis acid catalysts. Examples of suitable catalysts include aluminium chloride and iron (III) chloride. A preferred catalyst is aluminium chloride.

Typically, the ring closure reaction is carried out in the presence of a conventional solvent. Suitable solvents are those which have been described above for the chlorination reaction—with the exception of toluene—and the same solvent or mixture of solvents may be used for the ring closure reaction. Preferably, a solvent comprising a halogenated alkane such as dichloromethane is used for the ring closure reaction. Mixtures of a hydrocarbon solvent such as heptane and a halogenated solvent such as dichloromethane are particularly suitable for carrying out the ring closure reaction. Preferably, the ring closure reaction is carried out in a mixture of the hydrocarbon solvent which has been used for the chlorination reaction, such as heptane, and a halogenated solvent such as dichloromethane.

The ring closure reaction can be carried out in a wide temperature range. Typically, it is performed at from 0° C. up to 100° C., in particular at from room temperature up to 100° C. A practical temperature for carrying out the ring closure reaction at laboratory scale as well as at pilot plant scale is room temperature.

Typically, the molar ratio of Friedel-Crafts catalyst used in the invention process to ketone (II) is 1:1 to 3:1. Preferably, it is 1:1 to 1.5:1, more preferably 1.2:1 to 1.3:1.

A typical reaction time for the ring closure reaction is 15 minutes to 2 hours, although longer reaction times were observed in some experiments.

The invention process can be carried out using means and equipment well-known to a person skilled in this art.

The invention process is particularly suitable for preparing 2-substituted 1-indanones. Examples have been described below.

As is known to a person skilled in the art, the 1-indanones of formula I may be reduced to the corresponding indenes in an inert solvent in two reaction steps using a reducing agent and an acid dehydrating agent.

Thus, the present invention also pertains to a process for preparing indenes of formula III:

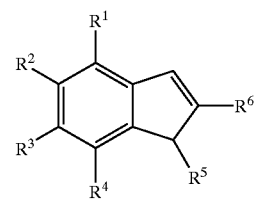

and isomers thereof, wherein $R^1$–$R^6$ have the meaning described above and which process is characterized in that a compound of formula II is converted into a compound of formula I according to the process described above, followed by reaction in an inert solvent first with a reducing agent and then with an acid dehydrating agent according to methods known per se.

Suitable reducing agents include sodium borohydride, lithium aluminium hydride, diisobutylaluminium hydride (DIBAL-H), and sodium bis(2-methoxyethoxy)aluminium hydride. For these and other suitable reducing agents the reader is referred to J. March, *Advanced Organic Chemistry*, Fourth Edition, John Wiley & Sons, New York, 1992, pp. 910–918. A particularly preferred reducing agent is DIBAL-H.

Suitable acids include sulfuric acid, methanesulfonic acid, p-toluenesulfonic acid, and phosphoric acid. For these and other suitable acids the reader is referred to J. March, *Advanced Organic Chemistry*, Fourth Edition, John Wiley & Sons, New York, 1992, pp. 1011–1012. A particularly preferred acid is p-toluenesulfonic acid.

Suitable solvents include alkanes such as pentane, hexane, heptane, toluene, and xylene, halogenated alkanes such as dichloromethane and chloroform, and ethers such as tetrahydrofuran.

The present invention is illustrated by the following Examples.

EXAMPLE 1

Synthesis of 2-methylindene

Preparation of 2-chloro-2-methylpropiophenone:

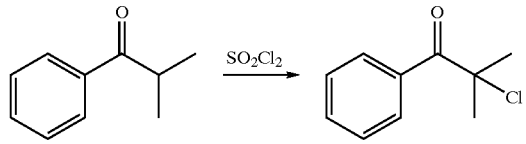

Isobutyrophenone (30.0 g, 0.20 mole) was dissolved in heptane (10 ml) and sulfuryl chloride (35 g, 0.26 mole) was added at once. After a few minutes gas evolution occurred. After 3 h of stirring at room temperature the reaction mixture was concentrated. The concentrate was dissolved in heptane (250 ml) and washed with 150 ml of an aqueous 2 wt % sodium bicarbonate solution. After drying over magnesium sulfate the solvent was removed under reduced pressure. The yield of 2-chloro-2-methylpropiophenone was 36.4 g or 98%.

¹H-NMR spectrum (400 MHz, CDCl₃): 1.86 (s, 6H), 7.42 (t, 2H), 7.53 (t, 1H), 8.13 (d, 2H).

Preparation of 2-methyl-1-indanone:

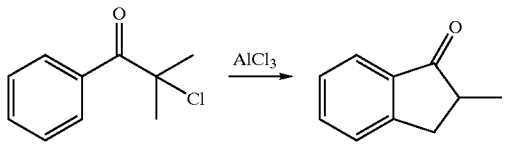

Aluminium chloride (45 g, 0.34 mole) was suspended in 200 ml of anhydrous dichloromethane. 2-Chloro-2-methylpropiophenone (30.0 g, 0.16 mole) in 30 ml of heptane was slowly added to this suspension. During the addition (30 min) the temperature was kept at room temperature. After the addition was completed, the reaction mixture was stirred overnight at room temperature.

The reaction mixture was poured onto 400 g of ice water, and the organic layer was separated. The organic layer was successively washed twice with an aqueous 5 wt % hydrochloric acid solution (100 ml) and once with an aqueous 2 wt % sodium bicarbonate solution (150 ml). After drying over anhydrous magnesium sulfate the solution was concentrated under reduced pressure. The yield of crude 2-methyl-1-indanone was 22.6 g or 94%. Distillation of the crude material gave 2-methyl-1-indanone as a light yellow liquid.

¹H-NMR spectrum (400 MHz, CDCl₃): 1.31 (d, 3H), 2.73 (m, 2H), 3.40 (dd, 1H), 7.36 (t, 1H), 7.45 (d, 1H), 7.58 (t, 1H), 7.75 (d, 1H).

Preparation of 2-methylindene:

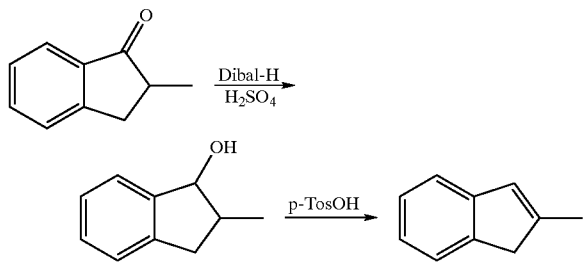

Diisobutylaluminium hydride (6 g, 42 mmoles) was added dropwise to 2-methyl-1-indanone (5.0 g, 34 mmoles) dissolved in 50 ml of anhydrous toluene, while the reaction temperature was kept at room temperature. The reaction mixture was stirred for 0.5 h after the addition. The reaction mixture was hydrolyzed by being added dropwise to sulfuric acid (aqueous 25 wt %, 50 ml) at 70° C. After the addition the aqueous layer was discarded, and the organic layer was washed twice with sulfuric acid (aqueous 5 wt %, 50 ml) and once with water (50 ml).

p-Toluenesulfonic acid (50 mg) was added to the organic layer, and the reaction mixture was heated under reflux with water separation for 1 h. After cooling to room temperature the organic layer was washed with sodium bicarbonate (aqueous 2 wt %, 50 ml), dried over magnesium sulfate, and carefully concentrated under reduced pressure. The yield of 2-methylindene was 4.2 g or 94%.

¹H-NMR spectrum (400 MHz, CDCl₃): 2.13 (s, 3H), 3.27 (s, 2H), 6.47 (s, 1H), 7.08 (d, 1H), 7.09–7.17 (m, 2H), 7.33 (d, 1H).

EXAMPLE 2

Synthesis of 2,4,6-trimethylindene

Preparation of 2,2',4'-trimethylpropiophenone:

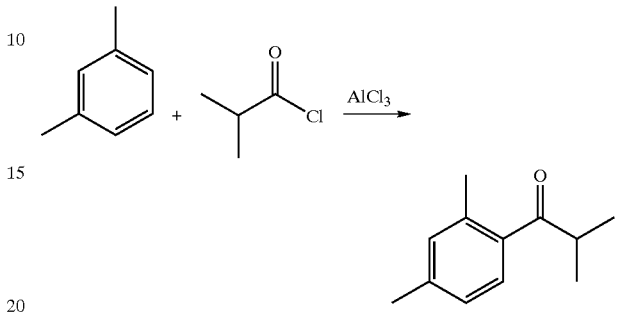

Aluminium chloride (28.0 g, 0.21 mole) was suspended in 200 ml of anhydrous dichloromethane and cooled to 0° C. A solution of m-xylene (21.2 g, 0.2 mole) and isobutyryl chloride (21.3 g, 0.20 mole) in 50 ml of anhydrous dichloromethane was slowly added to this suspension. After the addition was completed, the reaction mixture was stirred at 0° C. for 1 h.

The reaction mixture was poured onto 300 g of ice water, and the organic layer was separated. The organic layer was successively washed twice with a 5 wt % aqueous hydrochloric acid solution (150 ml) and once with a 2 wt % aqueous sodium bicarbonate solution (150 ml). After drying over anhydrous magnesium sulfate the solution was concentrated under reduced pressure. The yield of 2,2',4'-trimethylpropiophenone was 35.0 g or 99%.

¹H-NMR spectrum (400 MHz, CDCl₃): 1.17 (d, 6H), 2.35 (s, 3H), 2.41 (s, 3H), 3.37 (m, 1H), 7.03 (d, 1H), 7.04 (s, 1H), 7.48 (d, 1H).

Preparation of 2-chloro-2,2',4'-trimethylpropiophenone:

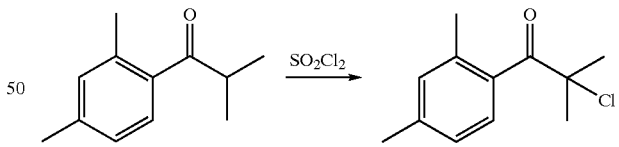

2,2',4'-Trimethylpropiophenone (30.0 g, 0.17 mole) was dissolved in heptane (10 ml), and sulfuryl chloride (35 g, 0.26 mole) was added at once. After about 5 min gas evolution occurred. After 3 h of stirring at room temperature the reaction mixture was concentrated. The concentrate was dissolved in heptane (200 ml) and was washed with 150 ml of a 2 wt % aqueous sodium bicarbonate solution. After drying over magnesium sulfate the solvent was removed under reduced pressure. The yield of 2-chloro-2,2',4'-trimethylpropiophenone was 35.5 g or 99%.

¹H-NMR spectrum (400 MHz, CDCl₃): 1.81 (s, 6H), 2.27 (s, 3H), 2.34 (s, 3H), 7.00 (d, 1H), 7.06 (s, 1H), 7.49 (d, 1H).

Preparation of 2,5,7-trimethyl-1-indanone:

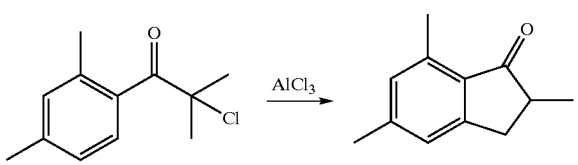

Aluminium chloride (38 g, 0.29 mole) was suspended in 200 ml of anhydrous dichloromethane. 2-Chloro-2,2',4'-trimethylpropiophenone (30.0 g, 0.14 mole) in 30 ml of heptane was slowly added to this suspension. During the addition (30 min) the temperature was kept at room temperature. After the addition was completed, the reaction mixture was stirred for 1 h at room temperature. The reaction mixture was poured onto 400 g of ice water, and the organic layer was separated. The organic layer was successively washed twice with a 5 wt % aqueous hydrochloric acid solution (150 ml) and once with a 2 wt % aqueous sodium bicarbonate solution (150 ml). After drying over anhydrous magnesium sulfate the solution was concentrated under reduced pressure. The yield of crude 2,5,7-trimethyl-1-indanone was 22.9 g or 92%. A sample was crystallized from pentane to give crystalline material.

$^1$H-NMR spectrum (400 MHz, CDCl$_3$): 1.27 (d, 3H), 2.36 (s, 3H), 2.58 (s, 3H), 3.25 (dd, 1H), 6.90 (s, 1H), 7.04 (s, 1H).

Preparation of 2,4,6-trimethylindene:

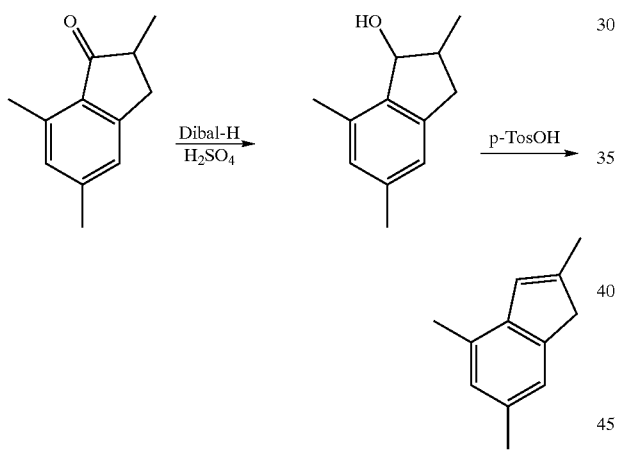

Diisobutylaluminium hydride (4.5 g, 32 mmoles) was added dropwise to a solution of 2,5,7-trimethyl-1-indanone (5.0 g, 29 mmoles) in 50 ml of anhydrous toluene, while the reaction temperature was kept at room temperature. The reaction mixture was stirred for 0.5 h after the addition. The reaction product was hydrolyzed by the reaction mixture being added dropwise to sulfuric acid (aqueous 25 wt %, 50 ml) at 70° C. After the addition the aqueous layer was discarded, and the organic layer was washed twice with sulfuric acid (aqueous 5 wt %, 50 ml) and once with water (50 ml).

p-Toluenesulfonic acid (50 mg) was added to the organic layer, and the reaction mixture was heated under reflux with water separation for 1 h. After cooling to room temperature the organic layer was washed with sodium bicarbonate (aqueous 2 wt %, 50 ml), dried over magnesium sulfate, and concentrated under reduced pressure. The yield of 2,4,6-trimethylindene was 4.4 g or 97%.

$^1$H-NMR spectrum (400 MHz, CDCl$_3$): 2.12 (s, 3H), 2.31 (s, 3H), 2.33 (s, 3H), 3.23 (s, 3H), 6.52 (s, 1H), 6.83 (s, 1H), 7.01 (s, 1H).

EXAMPLE 3

Synthesis of a Mixture of Tetrahydro-2-methylbenzindenes

Preparation of 2-methyl-1-(5,6,7,8-tetrahydro-2-naphthalenyl)-1-propanone:

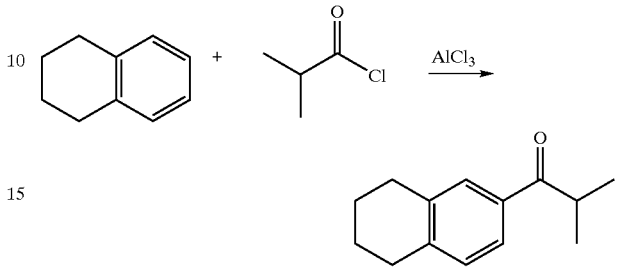

Aluminium chloride (28.0 g, 0.21 mole) was suspended in 200 ml of anhydrous dichloromethane (200 ml) and cooled to 0° C. A solution of 1,2,3,4-tetrahydronaphthalene (26.5 g, 0.2 mole) and isobutyryl chloride (21.3 g, 0.20 mole) in 50 ml of anhydrous dichloromethane was slowly added to this suspension. After the addition was completed, the reaction mixture was stirred at 0° C. for 1 h. The reaction mixture was poured onto 300 g of ice water, and the organic layer was separated. The organic layer was successively washed twice with a 5 wt % aqueous hydrochloric acid solution (150 ml) and once with a 2 wt % aqueous sodium bicarbonate solution (150 ml). After drying over anhydrous magnesium sulfate the solution was concentrated under reduced pressure. The yield of 2-methyl-1-(5,6,7,8-tetrahydro-2-naphthalenyl)-1-propanone was 39.7 g or 98%.

$^1$H-NMR spectrum (400 MHz, CDCl$_3$): 1.17 (d, 6H), 1.80 (m, 4H), 2.80 (m, 4H), 3.53 (m, 1H), 7.12 (d, 1H), 7.66 (m, 2H).

Preparation of 2-chloro-2-methyl-1-(5,6,7,8-tetrahydro-2-naphthalenyl)-1-propanone:

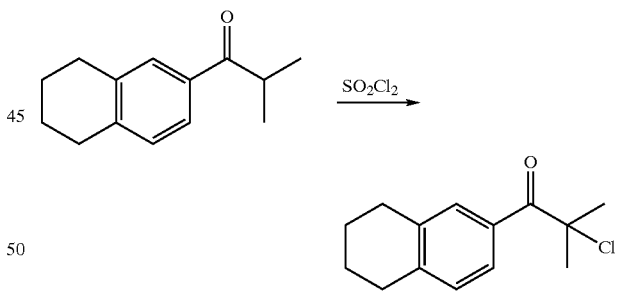

2-Methyl-1-(5,6,7,8-tetrahydro-2-naphthalenyl)-1-propanone (30.0 g, 0.15 mole) was dissolved in heptane (10 ml), and sulfuryl chloride (35 g, 0.26 mole) was added at once. After about 5 min gas evolution occurred. After 3 h of stirring at room temperature the reaction mixture was concentrated. The concentrate was dissolved in heptane (200 ml) and was washed with 150 ml of a 2 wt % aqueous sodium bicarbonate solution. After drying over magnesium sulfate the solvent was removed under reduced pressure. The yield of 2-chloro-2-methyl-1-(5,6,7,8-tetrahydro-2-naphthalenyl)-1-propanone was 34.5 g or 98%.

$^1$H NMR spectrum (400 MHz, CDCl$_3$): 1.80 (m, 4H), 1.87 (s, 6H), 2.81 (m, 4H), 7.06 (d, 1H), 7.84 (s, 1H), 7.90 (d, 1H).

Preparation of a mixture of 2,3,6,7,8,9-hexahydro-2-methyl-1H-benz[e]inden-1-one, 2,3,5,6,7,8-hexahydro-2-methyl-1H-benz[f]inden-1-one, and 1,2,6,7,8,9-hexahydro-2-methyl-3H-benz[e]inden-1-one:

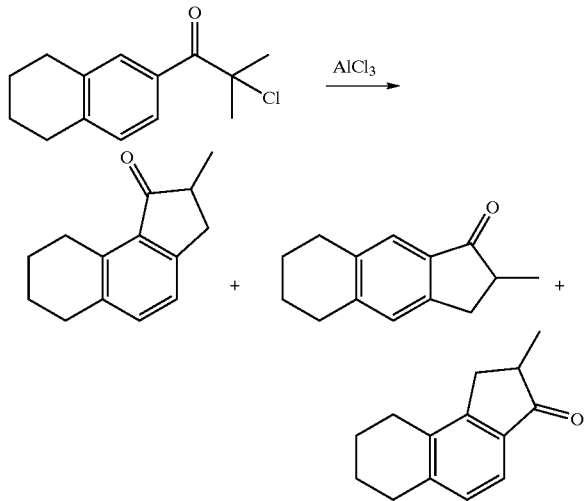

Aluminium chloride (35 g, 0.26 mole) was suspended in 200 ml of anhydrous dichloromethane. 2-Chloro-2-methyl-1-(5,6,7,8-tetrahydro-2-naphthalenyl)-1-propanone (30.0 g, 0.13 mole) in 30 ml of heptane was slowly added to this suspension. During the addition (30 min) the temperature was kept at room temperature. After the addition was completed, the reaction mixture was stirred for 1 h at room temperature. The reaction mixture was poured onto 400 g of ice water, and the organic layer was separated. The organic layer was successively washed twice with a 5 wt % aqueous hydrochloric acid solution (150 ml) and once with a 2 wt % aqueous sodium bicarbonate solution (150 ml). After drying over anhydrous magnesium sulfate the solution was concentrated under reduced pressure. The yield of the mixture of crude benzinden-1-ones was 24.5 g or 97%.

From the $^1$H-NMR spectrum, the molar ratio of the isomers was determined:

2,3,6,7,8,9-hexahydro-2-methyl-1H-benz[e]inden-1-one: 70%

2,3,5,6,7,8-hexahydro-2-methyl-1H-benz[f]inden-1-one: 24%

1,2,6,7,8,9-hexahydro-2-methyl-3H-benz[e]inden-1-one: 6%

A sample was crystallized from pentane to give crystalline 2,3,6,7,8,9-hexahydro-2-methyl-1H-benz[e]inden-1-one having a GC purity of 99.1 area %.

$^1$H-NMR spectrum (400 MHz, CDCl$_3$): 1.29 (d, 3H), 1.85 (m, 4H), 2.50 (dd, 1H), 2.68 (m, 3H), 2.80 (m, 2H), 3.20 (dd, 1H), 7.08 (d, 1H), 7.48 (d, 1H).

The crystallization filtrate was concentrated and analyzed by $^1$H NMR. The concentrate consisted mainly of a mixture of the two main isomers: the linear 2,3,5,6,7,8-hexahydro-2-methyl-1H-benz[f]inden-1-one and 2,3,6,7,8,9-hexahydro-2-methyl-1H-benz[e]inden-1-one. The $^1$H-NMR of the linear isomer was determined from the spectrum of the mixture of isomers.

$^1$H-NMR spectrum of 2,3,5,6,7,8-hexahydro-2-methyl-1H-benz[f]inden-1-one (400 MHz, CDCl$_3$): 1.28 (d, 3H), 1.85 (m, 4H), 2.68 (m, 4H), 2.80 (m, 2H), 3.31 (dd, 1H), 7.13 (s, 1H), 7.46 (s, 1H).

Preparation of 6,7,8,9-tetrahydro-2-methyl-3H-benz[e]indene:

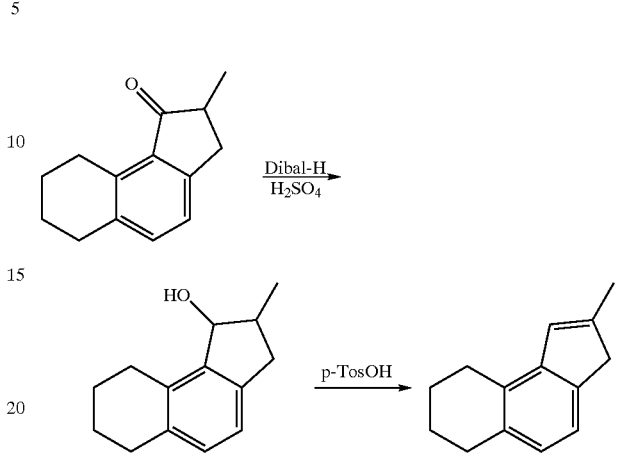

Diisobutylaluminium hydride (4.0 g, 28 mmoles) was added dropwise to a solution of 2,3,6,7,8,9-hexahydro-2-methyl-1H-benz[e]inden-1-one (5.0 g, 25 mmoles) in 50 ml of anhydrous toluene, while the reaction temperature was kept at room temperature. The reaction mixture was stirred for 0.5 h after the addition. The reaction product was hydrolyzed by sulfuric acid (aqueous 25 wt %, 50 ml) being added dropwise at 70° C. After the addition the aqueous layer was discarded, and the organic layer was washed twice with sulfuric acid (aqueous 5 wt %, 50 ml) and once with water (50 ml).

p-Toluenesulfonic acid (50 mg) was added to the organic layer, and the reaction mixture was heated under reflux with water separation for 1 h. After cooling to room temperature the organic layer was washed with sodium bicarbonate (aqueous 2 wt %, 50 ml), dried over magnesium sulfate, and concentrated under reduced pressure. The yield of crystalline 6,7,8,9-tetrahydro-2-methyl-3H-benz[e]indene was 4.4 g or 96%.

$^1$H NMR spectrum (400 MHz, CDCl$_3$): 1.79 (m, 4H), 2.11 (s, 3H), 2.66 (t, 2H), 2.77 (t, 2H), 3.05 (s, 2H), 6.40 (s, 1H), 6.92 (d, 1H), 7.00 (d, 1H).

Preparation of a mixture of 5,6,7,8-tetrahydro-2-methyl-1H-benz[f]indene and 6,7,8,9-tetrahydro-2-methyl-3H-benz[e]indene:

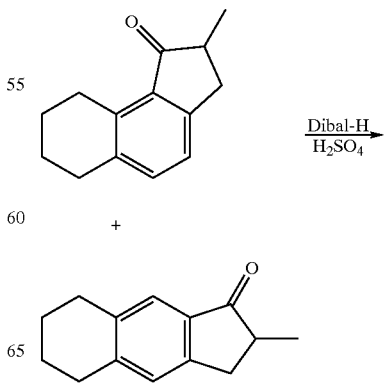

-continued

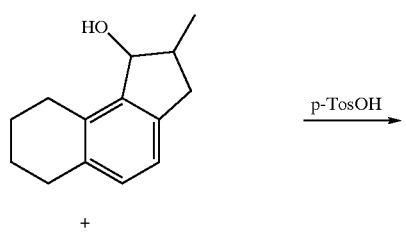

+

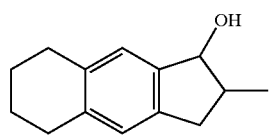

↓

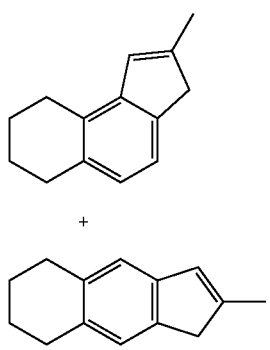

Diisobutylaluminium hydride (3.9 g, 27 mmoles) was added dropwise to a solution of a mixture of 2,3,5,6,7,8-hexahydro-2-methyl-1H-benz[f]inden-1-one and 2,3,6,7,8,9-hexahydro-2-methyl-1H-benz[e]inden-1-one (5.0 g, 25 mmoles) in 50 ml of anhydrous toluene, while the reaction temperature was kept at room temperature. The reaction mixture was stirred for 0.5 h after the addition. The reaction product was hydrolyzed by the reaction mixture being added dropwise to sulfuric acid (aqueous 25 wt %, 50 ml) at 70° C. After the addition the aqueous layer was discarded, and the organic layer was washed twice with sulfuric acid (aqueous 5 wt %, 50 ml) and once with water (50 ml).

p-Toluenesulfonic acid (50 mg) was added to the organic layer, and the reaction mixture was heated under reflux with water separation for 1 h. After cooling to room temperature, the organic layer was washed with sodium bicarbonate (aqueous 2 wt %, 50 ml), dried over magnesium sulfate, and concentrated under reduced pressure. The yield of 5,6,7,8-tetrahydro-2-methyl-1H-benz[e]indene and 6,7,8,9-tetrahydro-2-methyl-3H-benz[e]indene was 4.3 g or 93%.

The $^1$H-NMR of the linear isomer was determined from the spectrum of the mixture of isomers.

$^1$H-NMR spectrum of 5,6,7,8-tetrahydro-2-methyl-1H-benz[f]indene (400 MHz, CDCl$_3$): 1.79 (m, 4H), 2.10 (s, 3H), 2.75 (m, 4H), 3.21 (s, 2H), 6.38 (s, 1H), 6.93 (s, 1H), 7.05 (s, 1H).

EXAMPLE 4

Synthesis of 2-methyl-3H-benz[e]indene

Preparation of 2-methyl-1-(1-naphthalenyl)-1-propanone:

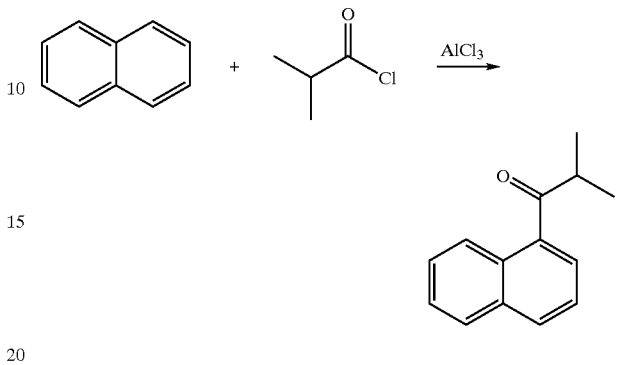

Aluminium chloride (28.0 g, 0.21 mole) was suspended in 200 ml of anhydrous dichloromethane and was cooled to −30° C. A solution of naphthalene (25.6 g, 0.2 mole) and isobutyryl chloride (21.3 g, 0.20 mole) in 50 ml of anhydrous dichloromethane was slowly added to this suspension. After the addition was completed, the reaction mixture was stirred at −30° C. for 1 h. The reaction mixture was then allowed to warm up to room temperature. The reaction mixture was poured onto 300 g of ice water, and the organic layer was separated. The organic layer was successively washed twice with a 5 wt % aqueous hydrochloric acid solution (150 ml) and once with a 2 wt % aqueous sodium bicarbonate solution (150 ml). After drying over anhydrous magnesium sulfate the solution was concentrated under reduced pressure. The yield of 2-methyl-1-(1-naphthalenyl)-1-propanone was 39.7 g or 98%.

$^1$H-NMR spectrum (400 MHz, CDCl$_3$): 1.25 (d, 6H), 3.51 (m, 1H), 7.46–7.60 (m, 3H), 7.73 (d, 1H), 7.87 (d, 1H), 7.95 (d, 1H), 8.33 (d, 1H).

Preparation of 2-chloro-2-methyl-1-(1-naphthalenyl)-1-propanone:

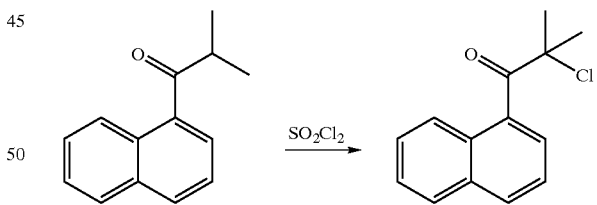

2-Methyl-1-(1-naphthalenyl)-1-propanone (30.0 g, 0.15 mole) was dissolved in heptane (10 ml), and sulfuryl chloride (30 g, 0.22 mole) was added at once. After about 5 min gas evolution occurred. After 3 h of stirring at room temperature the reaction mixture was concentrated. The concentrate was dissolved in heptane (200 ml) and washed with 150 ml of a 2 wt % aqueous sodium bicarbonate solution. After drying over magnesium sulfate the solvent was removed under reduced pressure. The yield of 2-chloro-2-methyl-1-(1-naphthalenyl)-1-propanone was 34.5 g or 98%.

$^1$H-NMR spectrum (400 MHz, CDCl$_3$): 1.89 (s, 6H), 7.42–7.58 (m, 3H), 7.74 (m, 1H), 7.79 (d, 1H), 7.88 (m, 1H), 7.92 (d, 1H).

Preparation of 2,3-dihydro-2-methyl-1H-benz[e]inden-1-one:

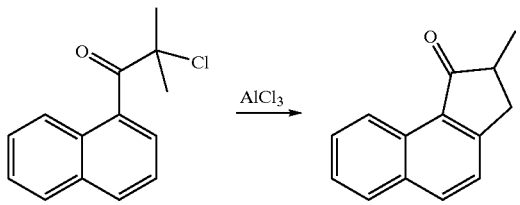

Aluminium chloride (35 g, 0.26 mole) was suspended in 200 ml of anhydrous dichloromethane. 2-Chloro-2-methyl-1-(1-naphthalenyl)-1-propanone (30.0 g, 0.13 mole) in 30 ml of heptane was slowly added to this suspension. During the addition (30 min) the temperature was kept at room temperature. After the addition was completed, the reaction mixture was stirred for 1 h at room temperature. The reaction mixture was poured onto 400 g of ice water, and the organic layer was separated. The organic layer was successively washed twice with a 5 wt % aqueous hydrochloric acid solution (150 ml) and once with a 2 wt % aqueous sodium bicarbonate solution (150 ml). After drying over anhydrous magnesium sulfate the solution was concentrated under reduced pressure. The yield of crude 2,3-dihydro-2-methyl-1H-benz[e]inden-1-one was 23.4 g or 93%. Distillation of the crude product under reduced pressure (b.p. 130° C., 0.5 mbar) gave 18.7 g (75%) of 2,3-dihydro-2-methyl-1H-benz[e]inden-1-one, which crystallized upon standing at room temperature.

$^1$H-NMR spectrum (400 MHz, CDCl$_3$): 1.37 (d, 3H), 2.80 (m, 2H), 3.45 (dd, 1H), 7.46 (d, 1H), 7.54 (t, 1H), 7.65 (t, 1H), 7.86 (d, 1H), 8.01 (d, 1H), 9.16 (d, 1H).

Preparation of 2-methyl-3H-benz[e]indene:

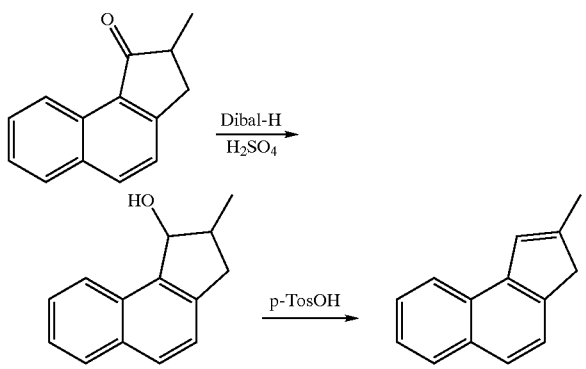

Diisobutylaluminium hydride (4.0 g, 28 mmoles) was added dropwise to a solution of 2,3-dihydro-2-methyl-1H-benz[e]inden-1-one (5.0 g, 26 mmoles) in 50 ml of anhydrous toluene, while the reaction temperature was kept at room temperature. The reaction mixture was stirred for 0.5 h after the addition. The reaction product was hydrolyzed by the reaction mixture being added dropwise to sulfuric acid (aqueous 25 wt %, 50 ml) at 70° C. After the addition the aqueous layer was discarded, and the organic layer was washed twice with sulfuric acid (aqueous 5 wt %, 50 ml) and once with water (50 ml).

p-Toluenesulfonic acid (50 mg) was added to the organic layer, and the reaction mixture was heated under reflux with water separation for 1 h. After cooling to room temperature the organic layer was washed with sodium bicarbonate (aqueous 2 wt %, 50 ml), dried over magnesium sulfate, and concentrated under reduced pressure. The yield of 2-methyl-3H-benz[e]indene was 4.1 g or 89%.

$^1$H-NMR spectrum (400 MHz, CDCl$_3$): 2.25 (s, 3H), 3.42 (s, 2H), 7.06 (s, 1H), 7.40 (t, 1H), 7.45 (t, 1H), 7.52 (d, 1H), 7.59 (d, 1H), 7.84 (d, 1H), 8.02 (d, 1H).

What is claimed is:

1. A process for preparing 1-indanones of formula I:

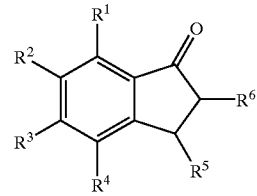

and isomers thereof, wherein $R^1$, $R^2$, $R^3$, $R^4$, $R^5$, and $R^6$ independently represent H or a $C_1$–$C_{20}$ hydrocarbon group or $R^1$ and $R^2$ or $R^2$ and $R^3$ or $R^3$ and $R^4$ and/or $R^5$ and $R^6$ together with the carbon atoms to which they are attached form a saturated or unsaturated 5- or 6-membered ring, said hydrocarbon group and/or said ring optionally containing one or more hetero atoms, said ring optionally being substituted with a $C_1$–$C_4$ hydrocarbon group, said process comprising reacting a compound of formula II:

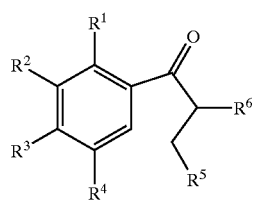

wherein $R^1$, $R^2$, $R^3$, $R^4$, $R^5$, and $R^6$ have the same meaning as defined above, with a chlorinating agent, followed by reaction with a Friedel-Crafts catalyst.

2. A process according to claim 1 wherein $R^1$, $R^2$, $R^3$, $R^4$, $R^5$, and $R^6$ independently represent H or a $C_1$–$C_{20}$ alkyl group or $R^1$ and $R^2$ or $R^2$ and $R^3$ or $R^3$ and $R^4$ and/or $R^5$ and $R^6$ together with the carbon atoms to which they are attached farm a saturated or unsaturated 5- or 6-membered ring, said ring optionally being substituted with a $C_1$–$C_4$ hydrocarbon group.

3. A process according to claim 1 or 2 wherein the molar ratio of ketone (II) to chlorinating agent is 1:1 to 1:2.

4. A process according to any one of claim 1 or 2 wherein the chlorinating agent is sulfuryl chloride.

5. A process according to any one of claim 1 or 2 wherein the molar ratio of Friedel-Crafts catalyst to ketone (II) is 1:1 to 3:1.

6. A process according to any one of claim 1 or 2 wherein the Friedel-Crafts catalyst is aluminum chloride or iron (III) chloride.

7. A process according to any one of claim 1 or 2, wherein the reaction with a Friedel-Crafts catalyst is carried out in a mixture of a hydrocarbon solvent and a halogenated alkane.

8. A process for preparing indenes of formula III:

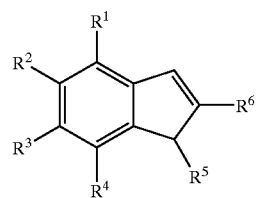

and isomers thereof, wherein $R^1$, $R^2$, $R^3$, $R^4$, $R^5$ and $R^6$ independently represent H or a $C_1$–$C_{20}$ hydrocarbon group or $R^1$ and $R^2$ or $R^2$ and $R^3$ or $R^3$ and $R^4$ and/or $R^5$ and $R^6$ together with the carbon atoms to which they are attached form a saturated or unsaturated 5- or 6-membered ring, said hydrocarbon group and/or maid ring optionally containing one or more hetero atoms, said ring optionally being substituted with a $C_1$–$C_4$ hydrocarbon group, characterized in that a compound of formula II is converted into a compound of formula I according to the process of any one of claim 1 or 2, followed by reaction in an inert solvent first with a reducing agent and then with an acid dehydrating.

9. A process according to claim 8 wherein the reducing agent is selected from the group consisting of sodium borohydride, lithium aluminum hydride, diisobutylaluminum hydride (DIBAL-H), and sodium bis(2-methoxyethoxy)aluminium hydride.

10. A process according to claim 8 wherein the acid is selected from the group consisting of sulfuric acid, methanesulfonic acid, p-toluenesulfonic acid, and phosphoric acid.

* * * * *

UNITED STATES PATENT AND TRADEMARK OFFICE
CERTIFICATE OF CORRECTION

PATENT NO.      : 6,548,710 B2
DATED           : April 15, 2003
INVENTOR(S)     : Woudenberg Page 1 of 1

It is certified that error appears in the above-identified patent and that said Letters Patent is hereby corrected as shown below:

Column 14,
Line 5, "farm" should read -- form --; and

Column 15,
Line 17, "maid" should read -- said --

Signed and Sealed this

Seventeenth Day of June, 2003

JAMES E. ROGAN
*Director of the United States Patent and Trademark Office*